United States Patent [19]

Fahmy

[11] Patent Number: 4,900,733
[45] Date of Patent: * Feb. 13, 1990

[54] N-ACYL PHOSPHONAMIDOTHIOATES AND DITHIOATES

[75] Inventor: Mohamed A. H. Fahmy, Wilmington, Del.

[73] Assignee: E. I. DuPont De Nemours & Co., Wilmington, Del.

[*] Notice: The portion of the term of this patent subsequent to Jul. 28, 2004 has been disclaimed.

[21] Appl. No.: 106,651

[22] Filed: Oct. 13, 1987

Related U.S. Application Data

[63] Continuation-in-part of Ser. No. 908,118, Sep. 16, 1986, abandoned.

[51] Int. Cl.$^4$ ............ A01N 57/02; C07F 9/44
[52] U.S. Cl. .................. 514/120; 558/171
[58] Field of Search ............ 514/120; 558/171, 178

[56] References Cited

U.S. PATENT DOCUMENTS

| | | | |
|---|---|---|---|
| 3,317,637 | 5/1967 | Brust | 558/178 |
| 3,868,449 | 2/1975 | Magee | 514/120 |
| 4,168,305 | 9/1979 | Maurer et al. | 514/120 |
| 4,544,553 | 10/1985 | Smolanoff et al. | 558/178 |
| 4,683,224 | 7/1987 | Fahmy | 514/120 |

OTHER PUBLICATIONS

Wustner et al., J. Ag. Food Chem., 26, at pp. 1104 to 1107 (1978).

Primary Examiner—Jacqueline V. Howard
Assistant Examiner—Margaret B. Medley
Attorney, Agent, or Firm—James A. Costello

[57] ABSTRACT

Certain N-acyl phosphonamidothioates and dithioates are useful as insecticides, acaricides and nematocides.

20 Claims, No Drawings

N-ACYL PHOSPHONAMIDOTHIOATES AND DITHIOATES

CROSS-REFERENCE TO RELATED APPLICATION

This application is a continuation-in-part of copending application U.S. Ser. No. 908,118 filed on Sept. 16, 1986, now abandoned.

BACKGROUND OF THE INVENTION

This invention relates to certain N-acyl phosphonamidothioates and dithioates, agriculturally suitable compositions containing them, and their use as insecticides, acaricides and nematocides.

U.S. Pat. No. 4,683,224 discloses insecticidal, acaricidal and nematocidal N-formyl phosphonamidothioates of the formula

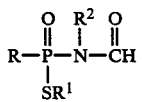

Wustner, et al., *J. Agric. Food Chem.* 26 (5) 1104 (1978) discloses insecticidal phosphonamidothioates of the formula

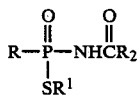

wherein R is $C_2$ alkyl; $R_1$ is $C_1$ to $C_2$ alkyl; and $R_2$ is $C_1$ to $C_5$ alkyl or $C_4$ alkenyl.

U.S. Pat. No. 4,168,305 discloses arthropodicidal and nematocidal dithiophosphonic acid ester-amides of the formula

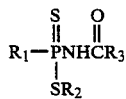

wherein $R_1$ is $C_1$ to $C_5$ alkyl; $R_2$ is $C_1$ to $C_6$ alkyl; and $R_3$ is $C_1$ to $C_6$ alkenyloxy or alkynyloxy, ($C_1$ to $C_3$ alkoxy)($C_1$ to $C_3$ alkoxy), phenoxy, halogenophenoxy, benzyloxy, $C_1$ to $C_6$ alkylamino, di($C_1$ to $C_2$ alkyl) amino, phenylamino, chlorophenylamino or alkylamino.

U.S. Pat. No. 3,317,637 discloses insecticidal, nematocidal and herbicidal N-haloacylphosphoric amides of the formula

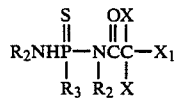

wherein each of $R_2$ is independently H or $C_1$ to $C_4$ alkyl; $R_3$ is $NHR_2$ or $C_1$ to $C_4$ alkoxy; each of X is independently Br or Cl; and $X_1$ is X or $C_1$ to $C_4$ alkyl.

U.S. Pat. No. 3,868,449 discloses insecticidal compositions containing N-acyl phosphonamidothioates of the formula

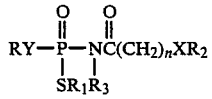

wherein R and $R_1$ are independently $C_1$ to $C_6$ alkyl, $C_1$ to $C_6$ alkenyl or $C_1$ to $C_6$ alkynyl; and X and Y are independently O or S; n is 1 to 6; $R_2$ is $C_1$ to $C_6$ alkyl, $C_6$ to $C_{10}$ aryl substituted by up to two F, Cl or Br; and $R_3$ is H or $C_1$ to $C_6$ alkyl.

U.S. Pat. No. 4,544,533 discloses arthropocidal phosphonamidothioates of the formula

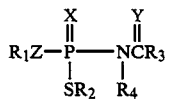

wherein $R_3$ is H, $CH_3$, carbo($C_1$ to $C_4$) alkoxy or thiocarbo($C_1$ to $C_4$) alkoxy; $R_4$ is, in part, H, unsubstituted or substituted $C_1$ to $C_7$ alkyl, unsubstituted or substituted $C_3$ to $C_6$ alkenyl; $C_3$ to $C_6$ alkynyl; unsubstituted or substituted phenyl or naphthyl, $C_1$ to $C_3$ alkyl; and X, Y and Z are independently O or S provided that both X and Y are not O at the same time except that, in the case that X and Y are both O and Z is S, then $R_1$ is n-$C_3H_7$ or $SC_4H_9$; $R_2$ is $SC_4H_9$; $R_5$ is H and $R_4$ is $CH_3$.

SUMMARY OF THE INVENTION

This invention comprises novel compounds of Formula I, agriculturally suitable compositions containing them, and their use as insecticides, acaricides and nematocides.

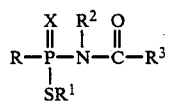

wherein

X is O or S;

R is selected from the group $C_1$ to $C_{10}$ alkyl, $C_2$ to $C_{10}$ alkenyl, phenyl and $C_7$ to $C_{10}$ phenalkyl;

$R^1$ is selected from the group $C_3$ to $C_6$ alkyl, $C_3$ to $C_6$ alkenyl, phenyl and $C_7$ to $C_{10}$ phenalkyl;

$R^2$ is selected from the group $C_1$ to $C_{10}$ alkyl, $C_2$ to $C_{10}$ alkenyl, $C_2$ to $C_{10}$ alkynyl, $C_1$ to $C_{10}$ haloalkyl, $C_3$ to $C_{10}$ alkoxycarbonylalkyl, $C_9$ to $C_{10}$ (alkoxycarbonyl)(phenyl) alkyl, phenyl, naphthyl, $C_7$ to $C_{10}$ phenalkyl and $C_8$ to $C_{10}$ phenalkenyl; and $R^3$ is selected from the group $C_1$ to $C_3$ alkyl and $C_1$ to $C_3$ haloalkyl.

The $R^2$ phenyl, naphthyl, phenalkyl and phenalkenyl groups can be substituted by one to three members of the group comprising halogen, $NO_2$, $NH_2$, $C_1$ to $C_4$ alkylamino, di($C_1$ to $C_4$) alkylamino, $C_1$ to $C_4$ alkylaminocarbonyl, di($C_1$ to $C_4$)alkylaminocarbonyl, CN, $C_1$ to $C_4$ alkyl, $C_1$ to $C_2$ haloalkyl, $C_1$ to $C_2$ alkoxy, $C_1$ to $C_2$ haloalkoxy, $C_1$ to $C_2$ alkylthio, $C_1$ to $C_2$ haloalkylthio, $C_1$ to $C_2$ alkylsulfonyl, and $C_1$ to $C_2$ haloalkylsulfonyl.

In the above definitions, the term "alkyl," used either alone or in compound words such as "alkylthio" or "haloalkyl," denotes straight chain or branched alkyl, e.g., methyl, ethyl, n-propyl, isopropyl or the different butyl isomers. Alkoxy denotes methoxy and ethoxy.

Alkenyl denotes straight chain or branched alkenes, e.g., 1-propenyl, 2-propenyl, 3-propenyl and the different butenyl isomers.

Alkynyl denotes straight chain or branched alkynes, e.g., ethynyl, 1-propynyl, 2-propynyl and the different butynyl isomers. Alkylsulfonyl denotes methylsulfonyl and ethylsulfonyl. Alkylthio, alkylamino, and the like are defined analogously.

The term "halogen," either alone or in compound words such as "haloalkyl," denotes fluorine, chlorine, bromine or iodine. Further, when used in compound words such as "haloalkyl" said alkyl can be partially halogenated for fully substituted with halogen atoms and said halogen atoms can be the same of different. Examples of haloalkyl include $CH_2CH_2F$, $CF_2CF_3$ and $CH_2CHFCl$.

The total number of carbon atoms in a substituent group is indicated by the $C_i$ to $C_j$ prefix where i and j are numbers from 1 to 10. For example, $C_1$ to $C_{10}$ alkyl would designate methyl through decyl.

Preferred for reasons that include greater insecticidal, acaricidal and nematocidal efficacy are:

Compounds of Formula I where
R is $C_1$ to $C_4$ alkyl;
$R^1$ is $C_3$ to $C_6$ alkyl;
$R^2$ is $C_1$ to $C_4$ alkyl, $C_3$ to $C_6$ alkoxycarbonylalkyl or benzyl optionally substituted by one to three of Cl or $OCH_3$;
$R^3$ is $CH_3$; and
X is 0.

DETAILS OF THE INVENTION

Compounds of Formula I can be prepared from the corresponding N-unsubstituted phosphonamidothioates and dithioates of the formula

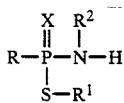

by one or more of the three procedures:

(a) treating a compound II with an appropriate anhydride

in the presence of a catalytic amount of sulfuric acid;

(b) treating a compound II with an appropriate acid chloride

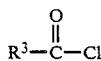

in the presence of a hydrogen chloride acceptor.

(c) converting a compound II to a metal salt (for example, the lithium salt), and treating the salt with an appropriate anhydride or acid chloride. Examples 5 to 9, illustrate this procedure wherein a suitable organo derivative of the metal, such as n-butyllithium, is slowly added to a solution of a precursor of Formula II in a suitable solvent, such as tetrahydrofuran (THF), at a low temperature, for example, $-50°$ C. to $-70°$ C., moisture and oxygen being excluded, then slowly adding the anhydride, and warming the mixture to complete the reaction.

Use of Procedure (a) is exemplified in Examples 1 to 3, wherein the reagents are brought together in an inert atmosphere, at room temperature, then concentrated sulfuric acid is added to catalyze the reaction. The reagents can be used neat, or it may be found to be desirable to employ an inert solvent. Suitable solvents include halogenated alkanes, such as methylene chloride.

Use of Procedure (b) is exemplified in Examples 2 and 4, wherein the reagents are brought together in an inert atmosphere at room temperature, then the mixture is cooled, and the hydrogen chloride acceptor is added. Preferably, to moderate the reaction, the acceptor is in solution in an inert solvent. Also, the reaction can be facilitated by use of a solvent. Suitable solvents are the halogenated alkanes, such as methylene chloride.

As shown in U.S. Pat. No. 4,391,760, the phosphonamidodithioate precursors (II, X is sulfur) can be prepared by treating the appropriate phosphonodithioic chloride of the formula

with the appropriate primary amine

The treatment can be conducted by adding a solution of the amine in a suitable solvent, such as acetone, to a solution of the chloride in a suitable solvent, such as acetone, at a low temperature such as 5° to 10° C., then allowing the mixture to come to room temperature, or warming it if necessary, and holding it at that temperature until the reaction is complete.

As shown in U.S. Pat. No. 4,391,760, and in U.S. Pat. No. 4,190,652, the chloride precursor can be prepared by treating a phosphonic dichloride of the formula

with the appropriate thiol, $R^1$—SH, in the presence of a solvent and an amine base, as hydrogen halide acceptor. Aromatic hydrocarbons, such as toluene, are suitable as the solvent. Any tertiary amine base is suitable, but the trialkylamines appear to be most suitable. Water should be excluded from the reaction mixture, as by using anhydrous reagents and conducting the treatment under nitrogen. Isolation of the product is effected by conventional techniques.

The phosphonamidothioate (II, X is oxygen) precursors can be prepared by a method analogous to that described by Cadogan, J. Chem. Soc. 3067, 1961, by treating the appropriate phosphonothioic chloride of the formula

with the appropriate primary amine of Formula VI. The treatment can be conducted by adding a solution of the amine in a suitable solvent, such as acetone, to a solution of the chloride in a suitable solvent, such as acetone, at a low temperature such as 5° to 10° C., then allowing the mixture to warm to room temperature, or warming it if necessary, and holding it at that temperature until the reaction is complete. It has been found that a higher yield of the desired product generally is obtained if water is excluded from the reaction system. Also, the phosphonamidothioate (II, X is oxygen) can be prepared as described in U.S. Pat. No. 3,636,206.

The phosphonothioic chloride precursor VIII can be prepared by a method analogous to that described in U.S. Pat. No. 4,190,652 and as described by Worms and Schmidt-Dunker, in "Organophosphorus Compounds", volume 7, page 42, 1976, Kosolapoff and Maier, editors, i.e., by treating a phosphonic dichloride of the formula

(IX)

with the appropriate thiol, $R^1$—SH, in the presence of a solvent and an amine base, as hydrogen chloride acceptor. Aromatic hydrocarbons, such as toluene, are suitable as the solvent. Any tertiary amine base is suitable, but the trialkylamines appear to be most suitable. Water should be excluded from the reaction mixture, as by using anhydrous reagents and conducting the treatment under nitrogen.

The phosphonothioic chloride of Formula VIII also can be prepared by the method described by Neimysheva, et al., Journal of General Chemistry, U.S.S.R. (English), 1966, volume 36, pages 520 to 525, i.e., by slowly adding the appropriate sulfenyl chloride

$R^1$—S—Cl           (X)

to a stirred solution of the appropriate phosphonous dichloride of the formula

R—P—Cl            (XI)
  |
  Cl in sulfur dioxide at a low temperature, e.g., −15° C. to −70° C., then warming the resulting mixture to room temperature, stripping it of volatiles and vacuum distilling the residue to give the product.

The preparations of particular individual species of the precursors VIII are described in application Ser. Nos. 777,378, 777,379 and 777,473.

The preparation, isolation and testing of individual species of the genus of Formula I, in particular instances, are described in the following examples. The identity of each of the products, and each of the precursors, was confirmed as necessary by appropriate chemical and spectral analyses.

EXAMPLE 1

S-(1-methylpropyl) N-acetyl-P-ethyl-N-methylphosphonamidothioate (1)

Under nitrogen, 30.7 ml of triethylamine was added over 10 minutes to a stirred mixture of 14.7 g of ethylphosphonic dichloride, 23.9 ml of 2-butanethiol and 125 ml of dry toluene at 5° to 10° C. The resulting mixture was stirred at 5° C. for 2 hours, then at room temperature for 15 hours, diluted with ether and filtered. The filtrate was washed with water, dried (Na$_2$SO$_4$) and stripped of solvent. Hexane was added to the residue and the mixture was washed with dilute aqueous bicarbonate solution, then with water, dried (Na$_2$SO$_4$), and stripped of solvent. The residue was distilled in a Kugelrohr apparatus to give S,S-bis(1-methylpropyl)ethylphosphonodithioate (1A).

Under nitrogen, a solution of 1.64 ml of sulfuryl chloride in 10 ml of carbon tetrachloride was added drop-by-drop over 36 minutes to a stirred solution of 5.09 g of 1A in 40 ml of carbon tetrachloride at 0° C. The resulting mixture was stirred at 0° C. for 7 minutes, for 1.5 hours at 5° C., then stripped of solvent under very low pressure, and the residue was distilled in a Kugelrohr apparatus to give S-(1-methylpropyl)ethylphosphonochloridothioate (1B), as a colorless liquid, b.p.: 70° C., 0.005 Torr.

Over 28 minutes, at 5° C., 2.7 g of methylamine was added to a solution of 8.0 g of 1B in 80 ml of dry ether. The resulting slurry was stirred at 5° C. for 2 hours, filtered, and the filtrate was stripped of solvent. The residue was dissolved in water, the solution was washed with hexane and extracted with methylene chloride. The extract was dried (Na$_2$SO$_4$) and stripped of solvent to give S-(1-methylpropyl)-P-ethyl-N-methylphosphonamidothioate (1C), as an amber liquid.

Under nitrogen, at room temperature, a mixture of 1.05 g of 1C, 10 ml of acetic anhydride and 2 drops of concentrated sulfuric acid was stirred for 4 days. A small amount of anhydrous sodium carbonate was added. A small amount of gas evolved, then methylene chloride was added and the resulting slurry was filtered. The solvent was stripped from the filtrate, and the residue was vacuum-chromatographed on silica gel, using ether, then ethyl acetate as eluent. 1 was obtained, as a yellow liquid.

EXAMPLE 2

S-(1-methylpropyl) N-(chloroacetyl)-P-ethyl-N-methylphosphonamidothioate (2)

A mixture of 1 g of 1C and 0.4 ml of chloroacetyl chloride was stirred for 70 minutes at room temperature under nitrogen. The mixture was cooled to 5° C. and a solution of 0.77 ml of triethylamine in 2 ml of dry methylene chloride was added dropwise over 4 minutes. The temperature of the mixture rose to 15° C. The mixture was stirred at room temperature for 4 days, then washed with water, dried (Na$_2$SO$_4$) and stripped of solvent. The residue was vacuum-chromatographed on silica gel, beginning with methylene chloride as eluent and gradually replacing it with ether, to give 1, as an amber liquid.

EXAMPLES 3 and 4

By the procedures of Examples 1 and 2, respectively, the following further individual species were prepared:

(a) S-propyl N-acetyl-P-ethyl-N-methylphosphonamidothioate (3), as a yellow liquid;

(b) S-propyl N-(chloroacetyl)-P-ethyl-N-methylphosphonamidothioate (4), as an amber liquid.

EXAMPLE 5

S-(1-dimethylethyl)
P-ethyl-N-methyl-N-propionylphosphonamidothioate
(5)

Butyllithium in the amount of 2.0 ml (1M in hexane) was added slowly dropwise to a solution of 0.64 g of S-(1,1-dimethylethyl) P-ethyl N-methylphosphonamidothioate in 8 ml of dry THF at −70° C. under nitrogen, then after 30 minutes at −70° C., 7.96 g of propionic anhydride was added dropwise and the mixture held at −70 C. for 2 hours. The resulting mixture was stripped of solvent, the residue was dissolved in a mixture of water and methylene chloride. The two liquid phases were separated, the organic phase was dried (MgSO4), filtered and stripped of solvent. The residue was flash-chromatographed on silica gel, using ethyl acetate as eluent; one set of fractions was stripped of volatiles under very low pressure, to give 5, as a very pale yellow liquid.

EXAMPLES 6 to 19

By the procedures described in Example 5, the following further individual species of the genus of Formula I were prepared and isolated, each species being identified in terms of the symbols of Formula I (X=0).

| Ex. No. | Cmpd. No. | R | $R^1$ | $R^2$ | $R^3$ |
|---|---|---|---|---|---|
| 6 | 6 | ethyl | 1,1-dimethylpropyl | methyl | methyl |
| 7 | 7 | ethyl | 1,1-dimethylethyl | methyl | methyl |
| 8 | 8 | methyl | propyl | methyl | methyl |
| 9 | 9 | ethyl | 1,1-dimethylethyl | methyl | ethyl |
| 10 | 10 | ethyl | 2-methylpropyl | methyl | ethyl |
| 11 | 11 | ethyl | 2-methylpropyl | methyl | methyl |
| 12 | 12 | methyl | 2-methylpropyl | methyl | ethyl |
| 13 | 13 | methyl | 1-methylpropyl | methyl | ethyl |
| 14 | 14 | methyl | propyl | methyl | ethyl |
| 15 | 15 | methyl | 2-methylpropyl | methyl | methyl |
| 16 | 16 | ethyl | 1,1-dimethylpropyl | 2-methylpropyl | ethyl |
| 17 | 17 | methyl | 1,1-dimethylpropyl | methyl | ethyl |
| 18 | 18 | ethyl | 1-methylethyl | methyl | methyl |
| 19 | 19 | ethyl | 1,1-dimethylpropyl | 2-methylpropyl | methyl |

EXAMPLE 20

S-(1methylpropyl)P-methyl-N-(1-ethoxycarbonyl)ethyl-N-acetylphosphonamidothioate Triethylamine (4.04 g, 0.04 m) was added dropwise to a mixture of S-(1-methylpropyl)ethylphosphonochloridotriote (3.73 g, 0.02 m), alanine ethyl ester hydrochloride (3.07 g, 0.02 m) and 4λ molecular sieves (4 g) in anhydrous ether (30 ml) under nitrogen. After 50 minutes, the reaction mixture was diluted with water and the layers were separated. The aqueous layer was extracted with methylene chloride and the combined organic solutions were dried over magnesium sulfate. Filtration, removal of solvent under reduced pressure and purification of the remaining material by flash column chromatography (silica gel, ethyl acetate) afforded S-(1-methylpropyl)P-methyl-N-(1-ethoxycarbonyl)ethylphosphonamidothioate (20A) as a pale yellow liquid (3.76 g).

The compound, n-butyllithium (2.8 ml of a 1.6M solution in hexane) was added dropwise to a solution of 20A (1.1 g, 0.0041 m) in anhydrous tetrahydrofuran (7 ml) at −70° C. under nitrogen. After 30 minutes, acetic anhydride (4.20 g, 0.0412 m) was added dropwise. After an additional 2 hours, the solvent was removed under reduced pressure and the remaining material dissolved in methylene chloride/water. The layers were separated and the aqueous phase extracted with additional methylene chloride. The combined organic solutions were then dried over magnesium sulfate. Filtration, removal of solvent under reduced pressure and purification of the remaining material by flash column chromatography (silica gel, ethyl acetate-hexane 1:1) afforded S-(1-methylpropyl)-P-methyl-N-(1-ethoxycarbonyl)ethyl-N-acetylphosphonamidothioate (20B) as a very pale yellow liquid (0.3 g).

EXAMPLES 21 to 29

By the procedures described in Example 20, the following species of the genus of Formula I were prepared and isolated, each species being identified in terms of the symbols of Formula I (X=0).

| Ex. No. | Cmpd. No. | R | $R^1$ | $R^2$ | $R^3$ |
|---|---|---|---|---|---|
| 21 | 21 | methyl | 1-methylpropyl | 1-(ethoxycarbonyl)ethyl | ethyl |
| 22 | 22 | ethyl | propyl | 2-methylpropyl | ethyl |
| 23 | 23 | methyl | 1-methylpropyl | 1-(ethoxycarbonyl)-2-phenylethyl | methyl |
| 24 | 24 | methyl | 1-methylpropyl | 1-(ethoxycarbonyl)-2-phenylethyl | ethyl |
| 25 | 25 | ethyl | 1-methylpropyl | methoxycarbonylmethyl | methyl |
| 26 | 26 | methyl | 1-methylpropyl | ethoxycarbonylmethyl | methyl |
| 27 | 27 | methyl | 1-methylpropyl | L-1-(ehhoxycarbonyl)ethyl | methyl |
| 28 | 28 | methyl | 1-methylpropyl | D-1-(ethoxycarbonyl)ethyl | methyl |
| 29 | 29 | ethyl | 1-methylpropyl | ethoxycarbonylmethyl | ethyl |

All of these species were obtained as pale yellow liquids, except Nos. 14 and 18 which were obtained as colorless liquids.

Compounds of Formula I have been found to be toxic with respect to invertebrate pests, by which is meant insects of the class Insecta and related classes of arthropods, such as the acarids (e.g., mites), ticks, spiders, wood lice and the like. In particular, they have been found to be highly toxic to mites. Some of the compounds act upon the insects very rapidly, i.e., they are "quick-knockdown agents", even though they may not be very toxic to the insects. Many of the compounds have been found to have excellent systemic activity. Still others possess very good residual activity in soil against soil pests such as the corn rootworm. Compounds of Formula I also have been found highly active against major nematode species.

For application, a compound of the invention ordinarily is applied most effectively by formulating it with a suitable inert carrier or surface-active agent, or both. The invention, therefore, also includes compositions suitable for combatting pests, such compositions comprising an inert carrier or surface-active agent, or both, and as active ingredient at least one compound of the invention. The invention also provides a method of combatting pests at a locus, which comprises applying to that locus a compound of the invention or a pesticidal composition according to the invention.

The term "carrier" as used herein means an inert solid or liquid material, which can be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, i.e., horticulturally acceptable adjuvants, are suitable.

Suitable solid carriers are natural and synthetic clays and silicates including natural silicas such as diatomaceous earths; magnesium silicates including talcs; magnesium aluminum silicates including attapulgites and vermiculites; aluminum silicates including kaolinites, montmorillonites and micas; calcium carbonate; calcium sulfate; synthetic hydrated silicon oxides and synthetic calcium or aluminum silicates; elements such as carbon and sulfur; natural and synthetic resins such as coumarone resins, polyvinyl chloride and styrene polymers and copolymers; bitumen; waxes such as beeswax, paraffin wax, and chlorinated mineral waxes; solid fertilizers including superphosphates; and ground, naturally-occurring fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent can be an emulsifying agent or a dispersing agent or a wetting agent; it can be non-ionic or ionic. Any of the surface-active agents usually applied in formulating herbicides or insecticides can be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and-/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention can be prepared as wettable powders, dusts, granules, solutions, emulsifiable concentrates, emulsions, suspension concentrates and aerosols. Wettable powders are usually compounded to contain 25 to 75% by weight of active compound and usually contain, in addition to the solid carrier, 3 to 10% by weight of a dispersing agent, 2 to 15% of a surface-active agent and, where necessary, 0 to 10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5 to 10% by weight of the active compound.

Granules are usually prepared to have a size between 10 and 100 BS mesh (1.676 to 0.152 mm), and can be manufactured by agglomeration or impregnation techniques. Generally, granules will contain 0.5 to 25% by weight of the active compound, 0 to 1% by weight of additives such as stabilizers, slow release modifiers and binding agents. Emulsifiable concentrates usually contain, in addition to the solvent and, when necessary, cosolvent, 10 to 50% weight per volume of the active compound, 2 20% weight per volume emulsifiers and 0 to 20% weight per volume of appropriate additives such as stabilizers, penetrants and corrosion inhibitors. Suspension concentrates are compounded so as to obtain a stable, non-sedimenting, flowable product and usually contain 10 to 75% weight of the active compound, 0.5 to 5% weight of dispersing agents, 1 to 5% of surface-active agent, 0.1 to 10% weight of suspending agents, such as defoamers, corrosion inhibitors, stabilizers, penetrants and stickers, and as carrier, water or an organic liquid in which the active compound is substantially insoluble; certain organic solids or inorganic salts can be dissolved in the carrier to assist in preventing sedimentation or as antifreeze agents for water.

Of particular interest in current practice are the water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or more by weight of finely divided active material, 3 to 7% by weight of a blend of surfactants, which act as wetting, dispersing, suspending and binding agents, 1 to 3% by weight of a finely divided carrier, which acts as a resuspending agent.

Aqueous dispersions and emulsions, for example, compositions obtained by diluting a wettable powder or a concentration according to the invention with water, also lie within the scope of the present invention. The said emulsions can be of the water-in-oil or of the oil-in-water type, and may have thick, mayonnaise-like consistency.

It is evident from the foregoing that this invention contemplates compositions containing as little as about 0.0001% by weight to as much as about 95% by weight of a compound of the invention as the active ingredient.

The compositions of the invention can also contain other ingredients, for example, other compounds possessing pesticidal, especially insecticidal, acaricidal or fungicidal properties, as are appropriate to the intended purpose.

The method of applying a compound of the invention to control pests comprises applying the compound, ordinarily in a composition of one of the aforementioned types, to the locus or area to be protected from the insects, such as the foliage and/or the fruit of plants and/or the soil around the plants or seeds. The compound, of course, is applied in an amount sufficient to effect the desired action. This dosage is dependent upon many factors, including the carrier employed, the method and conditions of the application, the type of pest to be controlled, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of the invention at the locus to be protected, i.e., the dosage which the insect contacts, is of the order of 0.001 to 0.5% based on the total weight of the formulation, though under some circumstances the effective concentration will be as little as 0.0001% or as much as 2%, on the same basis.

Activity of compounds of the invention with respect to insect and acarine pests was determined by using standardized test methods to measure the toxicity of the compounds as follows:

I. Houseflies (*Musca domestica* (Linne)) were tested by placing 50 4- to 5-day old adult houseflies into a spray cage and spraying with 0.6 ml of a solution of test compound. After spraying, the flies were observed to ascertain any knockdown effect, and then were anesthetized with $CO_2$ and transferred to a recovery cage containing a milk pad for food. The cages were held for 18 to 20 hours after which mortality counts were made. Both dead and moribund flies were counted. The tests were conducted employing several different dosage rates for each test compound.

II. Pea aphids (*Acyrthosiphon pisum* (Harris)) were tested by placing about 100 adult aphids on broad bean plants. The plants were sprayed with dilutions of an acetone solution of the test compound in water containing an emulsifier and held under laboratory conditions for 18 to 20 hours, at which time the living aphids on the plants were counted. The tests were conducted employing several different dosage rates for each test compound.

III. Adult female two-spotted spider mites (*Tetranychus urticae* (Koch)) were tested by placing 50 to 75 mites on the bottom side of leaves of pinto bean plants. The leaves were sprayed with dilutions of an acetone solution of the test compound in water containing an emulsifier and kept under laboratory conditions for about 20 hours, at which time mortality counts were made. The tests were conducted employing several different dosage rates for each compound.

IV. Third instar corn earworm larvae (*Heliothis zea* (Boddie)) were tested by spraying broad bean plants with dilutions of an acetone solution of the test compound in water containing an emulsifier. Immediately after spraying, 5 larvae were transferred to the plant and held for 44 to 46 hours, at which time the dead and moribund larvae were counted. The tests were conducted employing several different dosage rates for each test compound.

In each set of tests, identical tests were conducted using parathion as a standard for comparison. In each instance, the toxicity of the test compound was compared to that of parathion, the relative toxicity of the test compound then being expressed in terms of the relationship between the amount of the test compound and the amount of the standard pesticide required to produce the same percentage (50%) of mortality in the test insects. By assigning the standard pesticide an arbitrary rating of 100, the toxicity of the test compound was expressed in terms of the Toxicity Index, which compares the toxicity of the test compound of the invention with that of the standard pesticide. That is to say, a test compound having a Toxicity Index of 50 would be half as active, while one having a Toxicity Index of 200 would be twice as active, as the standard pesticide. The results are set forth in Table I.

TABLE I

| Cmpd. No. | Toxicity Index | | | |
|---|---|---|---|---|
| | Housefly | Pea Aphid | Corn Earworm | Spider Mite |
| 1 | 30 K[a] | 5 K | 20 K | 730 |
| 2 | 0 | 5 | 0 | 160 |
| 3 | (−b) | 30 | 5 | 550 |
| 4 | 0 | 0 | 0 | 20 |
| 5 | 20 K | 270 K | 20 | 2300 |
| 6 | 20 K | 900 K | 10 | 650 |
| 7 | 15 K | 20 K | 20 | 800 |
| 8 | 15 | 20 K | 140 | 500 |
| 9 | 10 | 15 K | 170 | 330 |
| 10 | 15 | 50 K | 0 | 160 |
| 11 | 15 | 50 K | 0 | 140 |
| 12 | 10 | 50 K | 15 | 350 |
| 13 | 20 | 50 K | 35 | 290 |

(a) K = rapid knockdown.
(b) − = not tested with respect to this species.

Many of the compounds of Formula I have been found to persist in the soil against soil pests, to have systemic activity and to have activity against nematodes. These types of activity are demonstrated by the following Examples.

V. Soil Activity against Southern Corn Rootworm. Test units (three replicates) were prepared by placing two germinated corn kernals on the surface of sassafrass loam soil in a small pot, spraying the unit with an acetone-water solution of the test compound at 1000 ppm, covering the seed with soil and placing 15 southern corn rootworm larvae in each pot. After 7 days, an evaluation of plant injury (1 to 5; 1=0%, 5=100%) and plant emergence (0 to 100 in % germination) is made. Results are tabulated below.

| Compound | Plant Injury | Plant Emergence |
|---|---|---|
| 1 | 1.0 | 38 |
| 25 | 1.0 | 100 |
| 27 | 1.4 | 88 |
| 29 | 1.4 | 88 |

VI. Systemic Activity. Turnip plants were infested with 80 to 100 green peach aphids and the bare turnip roots placed in a water-acetone solution of the test compound at 100 ppm. Mortality readings on the aphids were made at 48 hours and are reported on a percentage scale. The following results were obtained.

| Compound | % Mortality |
|---|---|
| 1 | 99 |
| 25 | 99 |

VII. Nematocidal Activity. Cucumber seeds are planted in a sand-soil mixture which has been inoculated with root knot nematode larvae. The test compound is applied to the sand-soil surface as an acetone-water solution at a rate which approximates 5 kg/ha. Twelve to fourteen days after treatment, the percent control of the nematodes is determined by comparing the number of knots on the test root system to the number of knots on an untreated, inoculated check. The following results were obtained.

| Compound | % Control |
| --- | --- |
| 1 | 100 |
| 27 | 100 |

The embodiments of the invention in which an exclusive property or privilege is claimed are defined as follows:

1. A compound of the formula

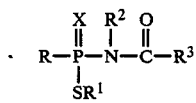

wherein:

X is O or S;

R is selected from the group $C_1$ to $C_{10}$ alkyl, $C_2$ to $C_{10}$ alkenyl, phenyl or $C_7$ to $C_{10}$ phenalkyl;

$R^1$ is selected from the group $C_3$ to $C_6$ alkyl, $C_3$ to $C_6$ alkenyl, phenyl or $C_7$ to $C_{10}$ phenalkyl;

$R^2$ is selected from the group $C_1$ to $C_{10}$ alkyl, $C_2$ to $C_{10}$ alkenyl, $C_2$ to $C_{10}$ alkynyl, $C_1$ to $C_{10}$ haloalkyl, $C_3$ to $C_{10}$ alkoxycarbonylalkyl, $C_9$ to $C_{10}$ (alkoxycarbonyl)(phenyl) alkyl, phenyl, naphthyl, $C_7$ to $C_{10}$ phenalkyl and $C_8$ to $C_{10}$ phenalkenyl; and $R^3$ is selected from the group $C_1$ to $C_3$ alkyl and $C_1$ to $C_3$ haloalkyl.

2. A compound according to claim 1 wherein:

R is $C_1$ to $C_4$ alkyl;

$R^1$ is $C_3$ to $C_6$ alkyl;

$R^2$ is $C_1$ to $C_4$ alkyl, $C_3$ to $C_6$ alkoxycarbonylalkyl or benzyl optionally substituted by one to three of Cl or $OCH_3$;

$R^3$ is $CH_3$; and

X is O.

3. A pesticidal composition comprising a pesticidally effective amount of a compound according to claim 1 and at least one of a carrier or surface-active agent.

4. A pesticidal composition comprising a pesticidally effective amount of a compound according to claim 2 and at least one of a carrier or surface-active agent.

5. A method for controlling a member from the group insects, acarids and nematodes comprising applying to the locus thereof an effective amount of a compound according to claim 1.

6. A method for controlling a member from the group insects, acarids and nematodes comprising applying to the locus thereof an effective amount of a compound according to claim 2.

7. A method for controlling a member from the group insects, acarids and nematodes comprising applying to the locus thereof an effective amount of a composition according to claim 3.

8. A method for controlling a member from the group insects, acarids and nematodes comprising applying to the locus thereof an effective amount of a composition according to claim 4.

9. A method according to claim 5 comprising controlling insects by applying said compound to their locus.

10. A method according to claim 5 comprising controlling acarids by applying said compound to their locus.

11. A method according to claim 5 comprising controlling nematodes by applying said compound to their locus.

12. A method according to claim 6 comprising controlling insects by applying said compound to their locus.

13. A method according to claim 6 comprising controlling acarids by applying said compound to their locus.

14. A method according to claim 6 comprising controlling nematodes by applying said compound to their locus.

15. A method according to claim 7 comprising controlling insects by applying said composition to their locus.

16. A method according to claim 7 comprising controlling acarids by applying said composition to their locus.

17. A method according to claim 7 comprising controlling nematodes by applying said composition to their locus.

18. A method according to claim 8 comprising controlling insects by applying said composition to their locus.

19. A method according to claim 8 comprising controlling acarids by applying said composition to their locus.

20. A method according to claim 8 comprising controlling nematodes by applying said composition to their locus.

* * * * *